United States Patent
Yamanaka et al.

(10) Patent No.: US 8,932,857 B2
(45) Date of Patent: *Jan. 13, 2015

(54) METHOD FOR SELECTING REDUCED DIFFERENTIATION RESISTANCE HUMAN INDUCED PLURIPOTENT STEM CELLS

(75) Inventors: Shinya Yamanaka, Kyoto (JP); Kazutoshi Takahashi, Kyoto (JP); Mari Ohnuki, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/704,584

(22) PCT Filed: Jun. 15, 2011

(86) PCT No.: PCT/JP2011/064195
§ 371 (c)(1),
(2), (4) Date: Dec. 14, 2012

(87) PCT Pub. No.: WO2011/158960
PCT Pub. Date: Dec. 22, 2011

(65) Prior Publication Data
US 2013/0089870 A1    Apr. 11, 2013

Related U.S. Application Data

(60) Provisional application No. 61/354,859, filed on Jun. 15, 2010.

(51) Int. Cl.
*C12N 5/00* (2006.01)
*C12N 5/074* (2010.01)

(52) U.S. Cl.
CPC ............ *C12N 5/0081* (2013.01); *C12N 5/0696* (2013.01); *C12N 2501/15* (2013.01); *C12N 2501/155* (2013.01)
USPC ............................... 435/377; 435/7.1; 435/39

(58) Field of Classification Search
None
See application file for complete search history.

(56) References Cited

U.S. PATENT DOCUMENTS

| 2008/0233610 | A1 | 9/2008 | Thomson et al. | |
| 2009/0068742 | A1 | 3/2009 | Yamanaka | |
| 2011/0028537 | A1 | 2/2011 | Thomson et al. | |
| 2012/0171717 | A1* | 7/2012 | Yamanaka et al. | 435/39 |

FOREIGN PATENT DOCUMENTS

| WO | WO 2007/069666 A1 | 6/2007 |
| WO | WO 2008/118820 A2 | 10/2008 |
| WO | WO 2010/137348 | 12/2010 |
| WO | WO 2011/019092 | 2/2011 |
| WO | WO 2011/027908 | 3/2011 |

OTHER PUBLICATIONS

International Preliminary Report on Patentability for International Application No. PCT/JP2011/064195, mailed on Jan. 3, 2013.
Chambers et al, "Highly efficient neural conversion of human ES and iPS cells by dual inhibition of SMAD signaling," *Nature Biotechnology*, vol. 27(3), pp. 275-280 (2009).
Cuny et al., "Structure-activity relationship study of bone morphogenetic protein (BMP) signaling inhibitors," *Bioorganic & Medicinal Chemistry Letters*, vol. 18(15), pp. 4388-4392 (2008).
Eiraku et al., "Self-Organized Formation of Polarized Cortical Tissues from ESCs and Its Active Manipulation by Extrinsic Signals," *Cell Stem Cell*, vol. 3(5), pp. 519-532 (2008).
Hao et al, "In Vivo Structure-Activity Relationship Study of Dorsomorphin Analogues Identifies Selective VEGF and BMP Inhibitors," *ACS Chemical Biology*, vol. 5(2), pp. 245-253 (2010).
Minowa et al., "Increase in tumour permeability following TGF-βtype I receptor-inhibitor treatment observed by dynamic contrast-enhanced MRI," *British Journal of Cancer*, vol. 101(11), pp. 1884-1890 (2009).
Miura et al., "Variation in the safety of induced pluripotent stem cell lines," *Nature Biotechnology*, vol. 27(8), pp. 743-745 (2009).
Oonuki et al., "Studies of differentiation-resistant cells in human induced-pluripotent stem (iPS) cells," *Regenerative Medicine*, vol. 10, Suppl., p. 201, IP-037 (2011).
Takahashi et al., "Induction of Pluripotent Stem Cells from Adult Human Fibroblasts by Defined Factors," *Cell*, vol. 131, pp. 861-872 (2007).
Tojo et al., "The ALK-5 inhibitor A-83-01 inhibits Smad signaling and epithelial-to-mesenchymal transition by transforming growth factor-β," *Cancer Science*, vol. 96(11), pp. 791-800 (2005).
Wada et al., "Highly Efficient Differentiation and Enrichment of Spinal Motor Neurons Derived from Human and Monkey Embryonic Stem Cells," *PLoS ONE*, vol. 4(8), e6722 (2009).
Watanabe et al., "A ROCK inhibitor permits survival of dissociated human embryonic stem cells," *nature biotechnology*, vol. 25(6), pp. 681-686 (2007).
Yamanaka, "A Fresh Look at iPS Cells," *Cell*, vol. 137(1), pp. 13-17 (2009).
Yu et al., "Induced Pluripotent Stem Cell Lines Derived from Human Somatic Cells," *SCIENCE*, vol. 318, pp. 1917-1920 (2007).
Araki, et al., "Primary evaluation of induced pluripotent stem cells using flow cytometry," *Inflammation and Regeneration*, vol. 33(1), pp. 3-12 (Jan. 2013).
Lin et al., "DNp73 improves generation efficiency of human induced pluripotent stem cells," *BMC Cell Biology*, vol. 13(1), pp. 1-7 (Mar. 2012).

(Continued)

*Primary Examiner* — Deborah Crouch
*Assistant Examiner* — Titilayo Moloye
(74) *Attorney, Agent, or Firm* — Knobbe, Martens, Olson & Bear, LLP (57) ABSTRACT

The present invention provides a method for selecting human induced pluripotent stem (iPS) cells which can be safely used for transplantation. That is, the present invention provides a method for selecting human iPS cells having reduced differentiation resistance, comprising the steps of: (1) inducing differentiation of human iPS cells; (2) detecting remaining undifferentiated cells after the step (1); and (3) selecting human iPS cells whose rate of remaining undifferentiated cells detected in step (2) is equivalent to or not more than that of control cells.

9 Claims, 5 Drawing Sheets

(56) References Cited

OTHER PUBLICATIONS

Liu, "iPS Cells: A More Critical Review," *Stem Cells and Development*, vol. 17(3), pp. 391-397 (2008).
Supplementary European Search Report for International Application No. PCT/JP2011064195, mailed on Nov. 7, 2013.
Office Action issued in European Patent Application No. 11795862.9 on Oct. 22, 2014.
Hu et al., "Neural differentiation of human induced pluripotent stem cells follows developmental principles but with variable potency," *PNAS*, vol. 107(9), pp. 4335-4340 (Mar. 2, 2010).

* cited by examiner

Fig. 1 iPS cells

Feeder-free/ 5 days

Undifferentiated condition/ 14 days

Counting the number of colonies

Fig. 2

Crystal violet staining

METHOD FOR SELECTING REDUCED DIFFERENTIATION RESISTANCE HUMAN INDUCED PLURIPOTENT STEM CELLS

TECHNICAL FIELD

The present invention relates to a method for selecting human induced pluripotent stem (iPS) cells which can be safely used for transplantation. More particularly, the present invention relates to a method for selecting human iPS cells having reduced differentiation resistance, comprising the steps of: (1) inducing differentiation of human iPS cells; (2) detecting remaining undifferentiated cells after the step (1); and (3) selecting human iPS cells whose rate of remaining undifferentiated cells detected in step (2) is equivalent to or not more than that of control cells.

BACKGROUND ART

In recent years, it has been reported that iPS cells are established by introduction of reprogramming-inducing genes into human skin-derived fibroblasts (WO 2007/069666 A1, Takahashi, K. et al., *Cell,* 131: 861-872 (2007), WO 2008/118820 A2 and Yu, J. et al., *Science,* 318: 1917-1920 (2007)). Since the iPS cells can be made to differentiate into cells of various tissues after being established from cells derived from the patient to be treated, they are expected to be useful as a graft material which does not cause the rejection reaction.

However, it was reported that, after inducing differentiation into neural progenitor cells, some mouse iPS cells remain undifferentiated and cause tumor formation when they are transplanted into mice (Miura K. et al., *Nat Biotechnol.,* 27: 743-745 (2009)). Such remaining of undifferentiated cells is considered to be due to properties of individual iPS cell lines. Further, since many cell lines are established at once by the process of establishing iPS cells, a simple method for selecting iPS cell lines suitable for transplantation among many iPS cell lines has been demanded.

SUMMARY OF THE INVENTION

An object of the present invention is to efficiently select safe human iPS cells suitable for clinical application. Specifically, an object of the present invention is to provide a method for selectively eliminating human iPS cells, in which the ratio of differentiation-resistant cells maintaining pluripotency after differentiation induction is high, from human iPS cells.

In order to solve the above objects, the inventors of the present invention induced differentiation of human iPS cells under an appropriate condition and then observed remaining undifferentiated cells which formed colonies culturing under an undifferentiation-maintaining condition or expressed Oct3/4 or TRA-1-60. As a result, it was found that the ratio of remaining undifferentiated cells was different among cell lines. For example, the number of colonies formed was low for human embryonic stem cells (ES cells) cultured under the above-described condition, while the number of colonies formed was large in some of human iPS cells.

From the above results, the inventors of the present invention discovered that human iPS cells having reduced differentiation resistance can be selected by inducing differentiation of human iPS cells under an appropriate condition and detecting remaining undifferentiated cells and selecting human iPS cells for which the number is low, thereby completed the present invention.

That is, the present invention is as follows.

[1] A method for selecting human induced pluripotent stem (iPS) cells having reduced differentiation resistance, said method comprising the steps of:
(1) inducing differentiation of human iPS cells;
(2) detecting remaining undifferentiated cells after the step (1); and
(3) selecting human iPS cells whose rate of remaining undifferentiated cells detected in step (2) is equivalent to or not more than that of control cells.

[2] The method according to [1], wherein differentiation induction is performed by culturing human iPS cells without using feeder cells.

[3] The method according to [2], wherein differentiation induction is performed by culturing human iPS cells in N2B27 medium.

[4] The method according to [3], wherein differentiation induction is performed by culturing human iPS cells in N2B27 medium for 5 days.

[5] The method according to [1], wherein detecting remaining undifferentiated cells is performed by measuring number of colonies formed after culturing under undifferentiation maintaining condition.

[6] The method according to [1], wherein differentiation induction in the step (1) is induction of differentiation to neural cells.

[7] The method according to [6], wherein the induction of differentiation to neural cells is performed by culturing human iPS cells with formation of embryoid bodies in the condition of serum free.

[8] The method according to [7], wherein the induction of differentiation to neural cells is performed by culturing human iPS cells in culture medium comprising BMP inhibitor and TGFβ family inhibitor.

[9] The method according to [8], wherein the BMP inhibitor is Dorsomorphin or LDN-193189, and the TGFβ family inhibitor is SB431542 or A-83-01.

[10] The method according to [1], wherein said control cells are human embryonic stem cells.

[11] The method according to [1], wherein said control cells are human iPS cells which is known to have reduced differentiation resistance.

By using the present invention, human iPS cells having reduced differentiation resistance, which are suitable for differentiation into cells to be used for transplantation, can be selected. Therefore, the present invention is very useful for application of human iPS cells to regenerative medicine.

BRIEF DESCRIPTION OF THE DRAWINGS

FIG. 3 shows the numbers of colonies observed after culturing the respective ES cell lines and iPS cell lines under undifferentiation-maintaining condition. Measurement of the colonies was independently carried out 3 times, and all of the results are shown. a represents the results obtained for human iPS cell lines established with 4 factors (OCT3/4, SOX2, KLF4 and c-MYC). b represents the results obtained for human iPS cell lines established with 3 factors (OCT3/4, SOX2 and KLF4). c represents the results obtained for human iPS cell lines established with 4 factors (OCT3/4, SOX2, KLF4 and c-MYC) from cells produced by differentiation induction of KhES1. KhES1 and KhES3 are ES cells used as controls. 201B2 and 201B7 are human iPS cells established with the 4 factors. 201B2-MF is a normal karyotype cell line selected from subclones of 201B2.

DESCRIPTION OF THE PREFERRED EMBODIMENTS

The present invention provides a method for selecting human iPS cells (human iPS cells) having reduced differentiation resistance, by inducing differentiation of human iPS cells and then detecting the remaining undifferentiated cells. The term "human iPS cells having reduced differentiation resistance" means human iPS cells in which the ratio of cells showing differentiation resistance is small. The term "cells showing differentiation resistance" herein means pluripotent stem cells in which the "self-renewal capacity" is abnormally strong among the two properties of stem cells, the "differentiation capacity" and the "self-renewal capacity". That is, the term means pluripotent stem cells have high risk of formation of a tumor because these cells still maintain pluripotency by self-renewal when they are induced to differentiate into the cells of interest and transplanted. In cases where such human iPS cells, in which the ratio of cells showing differentiation resistance is high, are induced to differentiate into the cells of interest and transplanted to a host, these cells may form a tumor with a possibility higher than that usually observed in cases where normal embryonic stem cells (ES cells) are used. On the other hand, in the "human iPS cells having reduced differentiation resistance" selected by the method of the present invention, the ratio of cells showing differentiation resistance is small, so that the risk of formation of a tumor is small when these cells are induced to differentiate into the cells of interest and transplanted to a host.

The human iPS cells which can be used for the selection method of the present invention are stem cells having pluripotency that allows differentiation of the cells into any cells existing in body and also having the self-renewal capacity.

I. Human Induced Pluripotent Stem Cells

Induced pluripotent stem (iPS) cells are artificial stem cells derived from somatic cells, which can be prepared by introducing certain particular nuclear reprogramming substances to somatic cells in the form of DNA or protein, and have properties almost equivalent to those of ES cells, such as pluripotency and growth capacity by self-renewal (K. Takahashi and S. Yamanaka (2006) Cell, 126: 663-676; K. Takahashi et al. (2007) Cell, 131: 861-872; J. Yu et al. (2007) Science, 318: 1917-1920; M. Nakagawa et al. (2008) Nat. Biotechnol., 26: 101-106; WO 2007/069666). The nuclear reprogramming substances may be genes specifically expressed in ES cells, or genes or gene products thereof that play important roles for maintaining the undifferentiated state of ES cells. The nuclear reprogramming substances are not restricted, and examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Sall1, Sall4, Glis1, Esrrb,Esrrg, Nr5a2 and Tbx3. These reprogramming substances may be used in combination when iPS cells are to be established. For example, the combination may contain at least one, two or three of the above reprogramming substances, and the combination preferably contains four of the above reprogramming substances.

The information on the nucleotide sequences of mouse and human cDNAs of the above-described respective nuclear reprogramming substances, and the amino acid sequences of the proteins encoded by the cDNAs can be obtained by referring to the NCBI (National Center for Biotechnology Information) accession numbers described in WO 2007/069666. Further, the information on the mouse and human cDNA sequences and amino acid sequences of L-Myc, Lin28, Lin28b, Esrrb and Esrrg can be obtained by referring to the NCBI accession numbers described below. Those skilled in the art can prepare desired nuclear reprogramming substances by a conventional method based on the information on the cDNA sequences or amino acid sequences.

| Gene name | Mouse | Human |
|---|---|---|
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |
| Nr5a2 | NM_030676 | NM_205860 |
| Tbx3 | NM_011535 | NM_005996 |

These nuclear reprogramming substances may be introduced into somatic cells in the form of protein by a method such as lipofection, binding to a cell membrane-permeable peptide, or microinjection, or in the form of DNA by a method such as use of a vector including a virus, plasmid and artificial chromosome; lipofection; use of liposomes; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (Proc Jpn Acad Ser B Phys Biol Sci. 85, 348-62, 2009). Examples of the artificial chromosome vector include human artificial chromosomes (HACs), yeast artificial chromosomes (YACs) and bacterial artificial chromosomes (BACs, PACs) (WO 2010/038904). Examples of the plasmid which may be used include plasmids for mammalian cells (Science, 322:949-953, 2008). The vectors may contain a regulatory sequence(s) such as a promoter, enhancer, ribosome binding sequence, terminator and/or polyadenylation site. Examples of the promoter to be used include the EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR and HSV-TK (herpes simplex virus thymidine kinase) promoter. Among these, the EF1α promoter, CAG promoter, MoMuLV LTR, CMV promoter, SRα promoter and the like are preferred. The vectors may further contain, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; or the like. Further, in order to remove, after introduction of the above vector into somatic cells, the genes encoding the nuclear reprogramming substances, or both the promoters and the genes encoding the reprogramming substances linked thereto, the vector may have loxP sequences in the upstream and the downstream of these sequences. In another preferred mode, a method may be employed wherein, after incorporation of the transgene(s) into a chromosome(s) using a transposon, transposase is allowed to act on the cells using a plasmid vector or an adenovirus vector, thereby completely removing the transgene(s) from the chromosome(s). Preferred examples of the transposon include piggyBac, which is a transposon derived from a lepidopteran insect (Kaji, K. et al., *Nature*, 458: 771-775 (2009); Woltjen et al., *Nature*, 458: 766-770 (2009); WO 2010/012077). Further, the vector may contain the origin of lymphotrophic herpes virus, BK virus or Bovine papillomavirus and sequences involved in their replication, such that the vector can replicate without incorporation into the chromosome and exist episomally. Examples of such a vector include vectors containing EBNA-1 and oriP sequences and vectors containing Large T and SV40ori sequences (WO 2009/115295; WO 2009/157201; WO 2009/149233). Further, in order to introduce plural nuclear reprogramming substances at the same time, an expression vector which allows polycistronic expression may be used. In order to allow polycistronic expression, the sequences encoding the genes may be linked to each other via IRS or the foot-and-mouth disease virus (FMDV) 2A coding region (*Science*, 322:949-953, 2008; WO 2009/092042 2009/152529).

For enhancing the induction efficiency of iPS cells upon the nuclear reprogramming, histone deacetylase (HDAC) inhibitors [for example, low molecular inhibitors such as valproic acid (VPA) (*Nat. Biotechnol.*, 26(7): 795-797 (2008)), trichostatin A, sodium butyrate, MC1293 and M344; and nucleic acid-type expression inhibitors such as siRNAs and shRNAs against HDAC (e.g., HDAC1 siRNA Smartpool (registered trademark) (Millipore) and HuSH 29 mer shRNA Constructs against HDAC1 (OriGene))], DNA methyltransferase inhibitors (e.g., 5'-azacytidine) (*Nat. Biotechnol.*, 26(7): 795-797 (2008)), G9a histone methyltransferase inhibitors [for example, low molecular inhibitors such as BIX-01294 (*Cell Stem Cell*, 2: 525-528 (2008)); and nucleic acid-type expression inhibitors such as siRNAs and shRNAs against G9a (e.g., G9a siRNA (human) (Santa Cruz Biotechnology))], L-channel calcium agonists (e.g., Bayk8644) (*Cell Stem Cell*, 3, 568-574 (2008)), p53 inhibitors [e.g., siRNAs and shRNAs against p53 (*Cell Stem Cell*, 3, 475-479 (2008))], Wnt Signaling activators (e.g., soluble Wnt3a) (*Cell Stem Cell*, 3, 132-135 (2008)), growth factors such as LIF, SCF and bFGF, ALK5 inhibitors (e.g., SB431542) (*Nat Methods*, 6: 805-8 (2009)), mitogen-activated protein kinase signaling inhibitors, glycogen synthase kinase-3 inhibitors (*PLoS Biology*, 6(10), 2237-2247 (2008)), miRNAs such as miR-291-3p, miR-294 and miR-295 (R. L. Judson et al., *Nat. Biotech.*, 27: 459-461 (2009)), and the like may be used in addition to the above-described factors.

Examples of the culture medium for induction of the iPS cells include (1) DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); (2) culture media for ES cells containing bFGF or SCF, for example, culture media for mouse ES cells (e.g., TX-WES medium, Thromb-X) and culture media for primate ES cells (e.g., culture medium for primate (human and monkey) ES cells, ReproCELL Inc., Kyoto, Japan).

Examples of the culture method include a method wherein somatic cells and nuclear reprogramming substances (DNAs or proteins) are brought into contact with each other at 37° C. in the presence of 5% $CO_2$ on DMEM or DMEM/F12 medium supplemented with 10% FBS, and the cells are cultured for about 4 to 7 days, followed by replating the cells on feeder cells (e.g., mitomycin C-treated STO cells, SNL cells or the like) and starting culture in a bFGF-containing culture medium for primate ES cells about 10 days after the contact between the somatic cells and the reprogramming substances, thereby allowing iPS-like colonies to appear about 30 to about 45 days after the contact, or later. To enhance the induction efficiency of iPS cells, the culture may be carried out under a condition wherein the concentration of oxygen is as low as 5 to 10%.

Alternatively, the somatic cells may be cultured on feeder cells (e.g., mitomycin C-treated STO cells or SNL cells) in DMEM medium supplemented with 10% FBS (which may further contain LIF, penicillin/streptomycin, puromycin, L-glutamine, non-essential amino acids, β-mercaptoethanol and/or the like, as appropriate), thereby allowing ES-like colonies to appear after about 25 to about 30 days of the culture, or later.

During the above culture, the culture medium is replaced with a fresh culture medium once a day from Day 2 of the culture. The number of the somatic cells used for nuclear reprogramming is not restricted, and usually within the range of about $5\times10^3$ to about $5\times10^6$ cells per 100-$cm^2$ area on the culture dish.

In cases where a gene including a drug resistance gene is used as a marker gene, cells expressing the marker gene can be selected by culturing the cells in a culture medium (selection medium) containing the corresponding drug. Cells expressing a marker gene can be detected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present description means cells derived from human, and examples thereof include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells) and pigment cells (e.g., retinal pigment epithelial cells), and progenitor cells (tissue progenitor cells) thereof. The level of differentiation of the cells and the age of the animal from which the cells are collected are not restricted, and either undifferentiated progenitor cells (including somatic stem cells) or terminally-differentiated mature cells may be used as the source of the somatic cells in the present invention. Here, examples of the undifferentiated progenitor cells include tissue stem cells (somatic stem cells) such as neural stem cells, hematopoietic stem cells, mesenchymal stem cells and dental pulp stem cells.

II. Differentiation Induction Step

"Differentiation induction" in the present invention includes not only differentiation into particular organ cells or progenitor cells thereof, but also differentiation into cell groups containing many kinds of cells such as endodermal cells, mesodermal cells and ectodermal cells. Examples of the organs into which differentiation is to be induced include, but are not limited to, skin, blood vessel, cornea, kidney, heart, liver, umbilical cord, intestine, nerve, lung, placenta, pancreas, brain, periphery of limbs, and retina. The method of such differentiation induction is not limited, and methods well-known to those skilled in the art may be used. Examples of the method include the method described in JP 2002-291469 A, which is a method for differentiation induction into neural stem cells; the method described in JP 2004-121165 A, which is a method for differentiation induction into pancreatic stem-like cells; and the method described in JP2003-505006, which is a method for differentiation induction into hematopoietic cells. Further examples of the method include the method described in JP2003-523766, which is a method for differentiation by formation of embryoid bodies.

A preferred method for differentiation induction in the present invention is a method for differentiation induction by culture without using feeder cells. More particularly, in this method, the cells are cultured in an arbitrary medium with a coated culture dish for adherent culture or floating culture with formation of embryoid bodies. Examples of the coating agent include collagen, gelatin, laminin, LIPIDURE (NOF Corporation) and Matrigel (BD), and combinations thereof. The coating agent is preferably LIPIDURE (NOF Corporation) or Matrigel (BD). Examples of the culture medium include, but are not limited to, Neurobasal medium (Invitrogen), minimum essential medium (MEM), Dulbecco's modified Eagle's medium (DMEM), RPMI1640 medium, 199 medium, F12 medium, and combinations thereof. The culture medium is preferably the combination of Neurobasal medium, DMEM and F12 medium. To these culture media, fetal bovine serum (FBS), albumin, transferrin, fatty acids, insulin, Knockout Serum Replacement (KSR) (Invitrogen), non-essential amino acids, nucleosides, L-glutamine, 2-mercaptoethanol, progesterone, putrescine, sodium selenite, bovine serum albumin fraction V (Invitrogen), vitamins, growth factors (excluding LIF, SCF and bFGF), antibiotics, antioxidants, pyruvic acid, buffering agents, inorganic salts, B27 supplement (Invitrogen), BMP inhibitor, TGF-β family inhibitor, Rho kinase (ROCK) inhibitor and the like may be added as appropriate, but it is preferred not to add LIF, SCF or bFGF. Examples of a BMP inhibitor having such properties include a compound that inhibits BMP2, BMP4, BMP6 or BMP7 capable of activating a transcription factor SMAD1, SMAD5, or SMAD8, such as Dorsomorphin (that is, 6-[4-(2-piperidin-1-yl-ethoxy)phenyl]-3-pyridin-4-yl-pyrazolo[1,5-a]pyrimidine) and a derivative thereof (P. B. Yu et al. (2007), Circulation, 116: II_60; P. B. Yu et al. (2008), Nat. Chem. Biol., 4: 33-41; J. Hao et al. (2008), PLoS ONE (www. plozone. org), 3 (8): e2904). Dorsomorphin is commercially available from Sigma-Aldrich, for example. Dorsomorphin has biological activity to inhibit the above BMP signaling by inhibiting the binding of BMP to a BMP receptor. In addition to them, examples of a BMP I-type receptor kinase inhibitor include LDN-193189 (that is, 4-(6-(4-(piperazin-1-yl)phenyl)pyrazolo[1,5-a]pyrimidin-3-yl)quinoline) and a derivative thereof (Yu PB et al. Nat Med, 14: 1363-9, 2008). Examples of a TGF-β family inhibitor include SB431542, SB202190 (R. K. Lindemann et al., Mol. Cancer 2: 20 (2003)), SB505124 (GlaxoSmithKline), NPC30345, SD093, SD908, SD208 (Scios), LY2109761, LY364947, and LY580276 (Lilly Research Laboratories), and A-83-01(WO 2009146408). SB431542 or A-83-01 is preferred. Examples of a ROCK inhibitor include Y-27632 (Calbiochem; water soluble) and Fasudil (HA1 077: Calbiochem). The cell density of the human iPS cells to be used for the differentiation induction is not restricted, and examples thereof include 1000000 to 3000000 cells/33.5 mm-dish (6-well plate), such as about 2500000 cells/33.5 mm-dish, about 2000000 cells/33.5 mm-dish, about 1500000 cells/33.5 mm-dish or about 1000000 cells/33.5 mm-dish. The cell density is particularly preferably about 2500000 cells/33.5 mm-dish (6-well plate). The period of differentiation culture is not restricted, and examples thereof include 2 to 14 days (e.g., 14days, 12days, 10 days, 8 days, 6 days, 4 days or 2 days). In the case of using N2B27 medium, the period of differentiation culture is preferably about 5 days. In another embodiment of using culture medium comprising BMP inhibitor and TGF-β family inhibitor, the period of differentiation culture is preferably about 14 days.

III. Step of Culturing under Undifferentiation-Maintaining Condition

Subsequently, in order to detect the differentiation resistance, the differentiation induced cells are cultured under an undifferentiation-maintaining condition. The undifferentiation-maintaining condition in the present invention is a condition under which human iPS cells can grow while maintaining their pluripotency, and examples thereof include culturing cells together with feeder cells. The culture medium is not restricted, and examples thereof include minimum essential medium (MEM), Dulbecco's modified Eagle's medium (DMEM), RPMI1640 medium, 199 medium, F12 medium or combinations of these, supplemented with 20% KSR, to which L-glutamine, non-essential amino acids, nucleosides, and/or 2-mercaptoethanol are added. In these cases, LIF, SCF or bFGF; 2i (an inhibitor of mitogen-activated protein kinase signalling and glycogen synthase kinase-3, *PLoS Biology*, 6(10), 2237-2247 (2008)); or the like may be added to the culture medium.

When the culture condition is changed from the differentiation inducing condition to the undifferentiation maintaining condition, the cells may be detached from the dish and then plated again. When this replating is carried out, only live cells may be selected. The method of selection of the live cells is not restricted, and it may be carried out by, for example, staining the cells with propidium iodide (PI) and separating/purifying unstained cells by FACS or the like.

The culture period under the undifferentiation maintaining condition is not restricted as long as colonies can be observed during the period, and preferably 10 days to 20 days, more preferably about 14 days.

The density of the cells upon culturing under the undifferentiation maintaining condition is not restricted, and examples thereof include 1000000 to 2500000 cells/33.5 mm-dish (6-well plate), such as about 2500000 cells/33.5 mm-dish, about 2000000 cells/33.5 mm-dish, about 1500000 cells/33.5 mm-dish or about 1000000 cells/33.5 mm-dish. The cell density is preferably about 1500000 cells/33.5 mm-dish (6-well plate).

In the case of directly detecting the undifferentiated cells, this step of culturing under undifferentiation-maintaining condition may be skipped.

IV. Step of Detecting Remaining Undifferentiated Cells

After the induction of differentiation of the cells, remaining undifferentiated cells can be detected using properties specific to the undifferentiated cells. Examples of such specific properties include formation of colonies after culturing under the undifferentiation maintaining condition as described above, expression of undifferentiation-specific antigens and expression of undifferentiation-specific genes. The undifferentiation-specific antigens are not restricted, and may be selected from, for example, the group consisting of SSEA-3, SSEA-4, TRA-1-60 and TRA-1-81. Examples of the undifferentiation-specific genes include the genes such as Oct3/4, Nanog and Rex1 described in WO2007/069666. The detection of remaining undifferentiated is performed by measuring number of undifferentiated cells and number of total cells. More preferably, the detection is ratio of number of undifferentiated cells to number of total cells.

In view of simplicity and providing sufficient sensitivity and specificity, it is preferred to observe formation of colonies to detect the generation of undifferentiated cells. The method of measurement of colonies is not restricted, and for example, the colonies are counted under the microscope and the counted number is used for the evaluation. When the colonies are measured, a staining such as crystal violet staining may be used. This measurement may be carried out either mechanically or visually.

On the other hand, cells expressing an undifferentiation-specific antigen or gene may be evaluated as the number of cells expressing the antigen or gene, using FACS. The method for detecting expression of an undifferentiation-specific gene is not restricted, and examples thereof include methods for detecting its transcription product (hnRNA, mRNA or the like), such as the PCR method, LAMP method and Northern hybridization method; and methods for detecting its translation product (peptide, modified peptide or the like), such as the RIA method, IRMA method, EIA method, ELISA method, LPIA method, CLIA method and immunoblotting.

V. Step of Selecting Human iPS Cells Having Reduced Differentiation Resistance (A) Selection Method by Absolute Evaluation After the induction of differentiation of the cells, the remaining undifferentiated cells are preferably evaluated as the number of colonies formed; the number of undifferentiation-specific-antigen-positive cells or the number of cells expressing an undifferentiation-specific gene; or the amount of an undifferentiation-specific antigen or the expression level of an undifferentiation-specific gene in a certain number of cells.

For iPS cells to be selected, the ratio of undifferentiated cells is preferably not more than 5%, 1%, 0.1%, more preferably not more than 1% with respect to the number of the cells cultured under an undifferentiation maintaining condition. The number of undifferentiated cells is especially preferably 0.

(B) Selection Method by Relative Evaluation

When the human iPS cells having reduced differentiation resistance are selected, human iPS cells, in which the degree of remaining undifferentiated cells is not more than that of undifferentiated cells obtained by inducing differentiation of ES cells and culturing the ES cells under an undifferentiation-maintaining condition, may be selected as the human iPS cells having reduced differentiation resistance.

Alternatively, the ratio in an available arbitrary human iPS cell line in which the state of differentiation resistance (ratio of undifferentiated cells) is preliminarily determined is investigated to prepare Table 1, and a value preliminarily set such that both the sensitivity and the specificity shown in Table 1 are not less than 0.9, preferably not less than 0.95, more preferably not less than 0.99 may be used as the control value. Both of the sensitivity and specificity values are still more preferably 1. Here, the fact that both the sensitivity and the specificity are 1 means that the control value is ideal since there is neither false positive nor false negative at all.

TABLE 1

| | Number of human iPS cell lines which do not show differentiation resistance | Number of human iPS cell lines showing differentiation resistance |
|---|---|---|
| Number of cell lines showing values higher than the control value | A | C |
| Number of cell lines showing values not more than the control value | B | D |
| | Sensitivity = B/(A + B) | Specificity = C/(C + D) |

The present invention will now be described more concretely by way of Examples, but, needless to say, the present invention is not restricted to these.

EXAMPLES

Example I

Cells

Human ES cells (KhES-1 and KhES-3) were received from Institute for Frontier Medical Sciences, Kyoto University, and cultured by a conventional method (Suemori H, et al. *Biochem Biophys Res Commun.* 345:926-32, 2006).

Human iPS cells were prepared from fibroblasts or dental pulp stem cells using 4 factors (OCT3/4, SOX2, KLF4 and c-MYC) or 3 factors (OCT3/4, SOX2 and KLF4) by conventional methods (Takahashi K, et al. *Cell.* 131:861-72, 2007; WO 2009/057831; WO 2010/013359; Nakagawa M, et al. *Nat Biotechnol.* 26:101-6, 2008). In the four-factor method, 22 lines of iPS cells such as 201B2 and 201B7 were used. In the three-factor method, 14 lines of iPS cells were used. By investigating the karyotypes of 201B2 and 201B7, it was confirmed that 201B2 shows trisomy of chromosome 12. On the other hand, the karyotype of 201B7 was normal. Among subclones of 201B2, 201B2-MF was established as a clone having the normal karyotype.

In terms of iPS cells derived from human ES cells (iPS-KhES1-Fib-4F), KhES1 was cultured in a bFGF-free culture medium in the absence of feeder cells for 5 days, and OCT3/4, SOX2, KLF4 and c-MYC were introduced to the cultured cells by the method described in Takahashi K, et al. *Cell.* 131:861-72, 2007 using a retrovirus, thereby 7 lines were established.

Differentiation Induction

Human ES cells, human iPS cells, or iPS cells derived from human ES cells were detached from the culture dish using CTK solution, which is PBS containing 0.1 mg/ml collagenase IV (Invitrogen), 0.25% trypsin (Invitrogen), 0.1 mM $CaCl_2$ (Nacalai Tesque) and 20% KSR (Invitrogen), and Accutase, and plated on a 6-well plate coated with BD Matrigel (BD) at a density of $2\times10^6$ cells/well. Subsequently, adherent culture was carried out using N2B27 medium for 5 days. N2B27 medium was prepared by the method described in Ying Q L, et al., *Nature Biotechnology* 21:183-186, 2003.

Culture Under Undifferentiation Maintaining Condition

Figure 1:
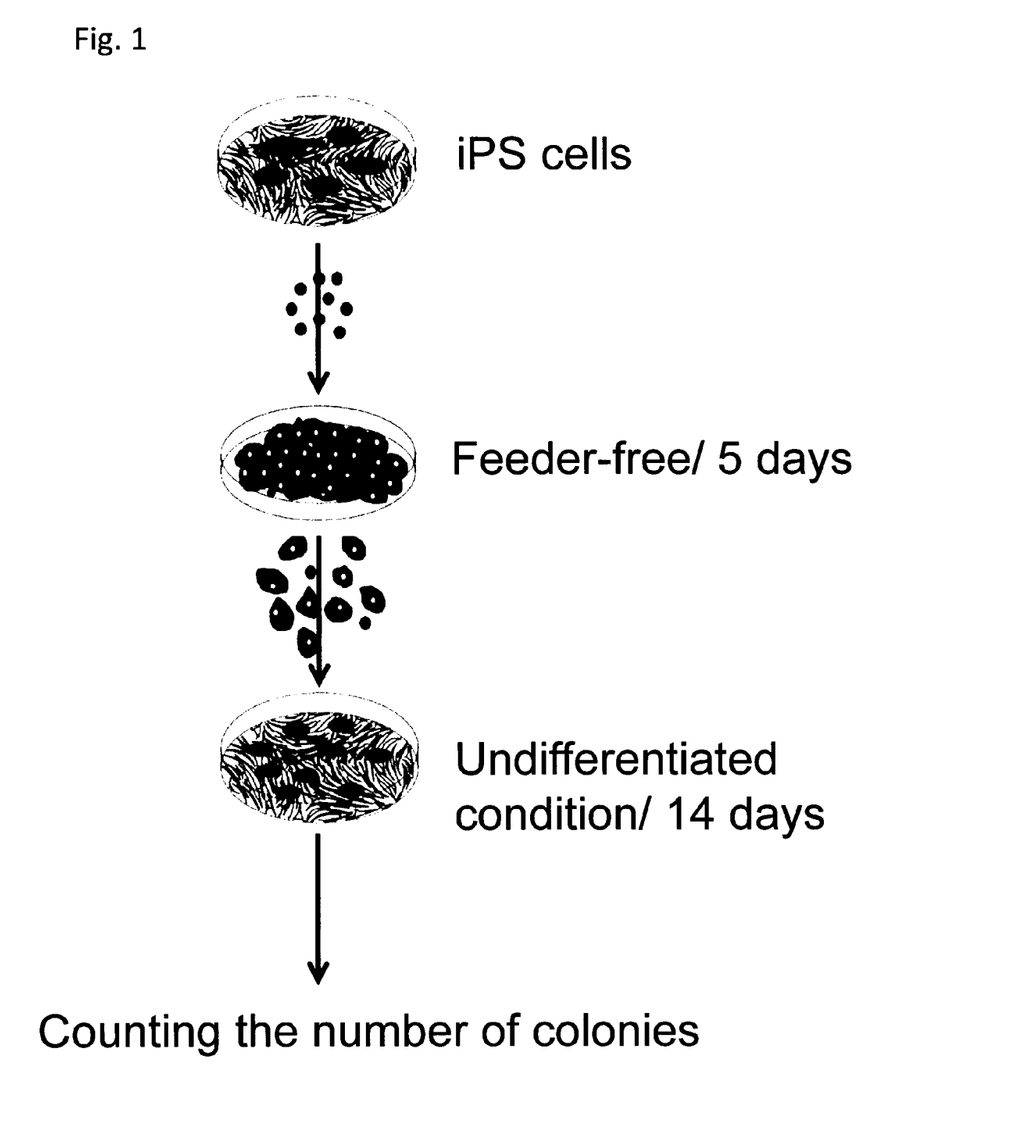
FIG. 1 shows the protocol of the experiment.

The cells whose differentiation was induced by the method described above were suspended using CTK solution, and plated on SNL cells at a density of $1.5\times10^6$ cells/10 cm-dish. Subsequently, the cells were cultured by adherent culture for 14 days using a culture medium for human ES cells, which is DMEM/F 12 containing 0.1 mM 2-mercaptoethanol (Sigma), non-essential amino acids (Invitrogen), 5 ng/ml recombinant human basic FGF (Upstate) and 20% KSR. The above culturing procedure is shown in FIG. 1.

Measurement of Number of Colonies Formed

Figure 2:
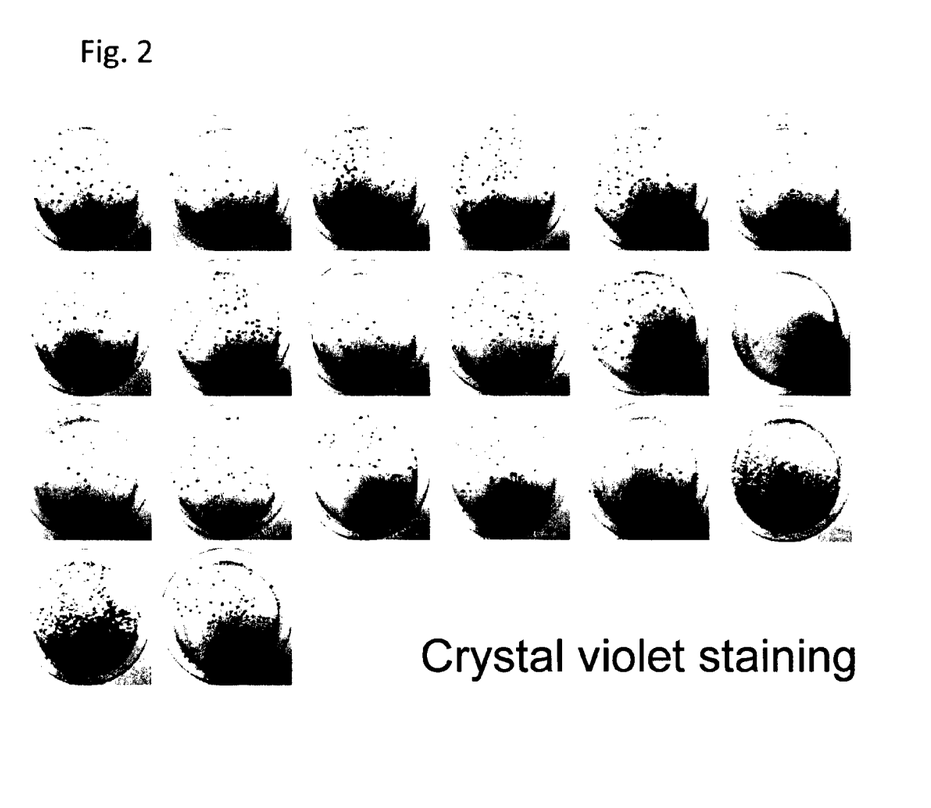
FIG. 2 shows the state of colonies observed with crystal violet staining, after differentiation induction and culturing under an undifferentiation-maintaining condition (photograph).
Figure 3:
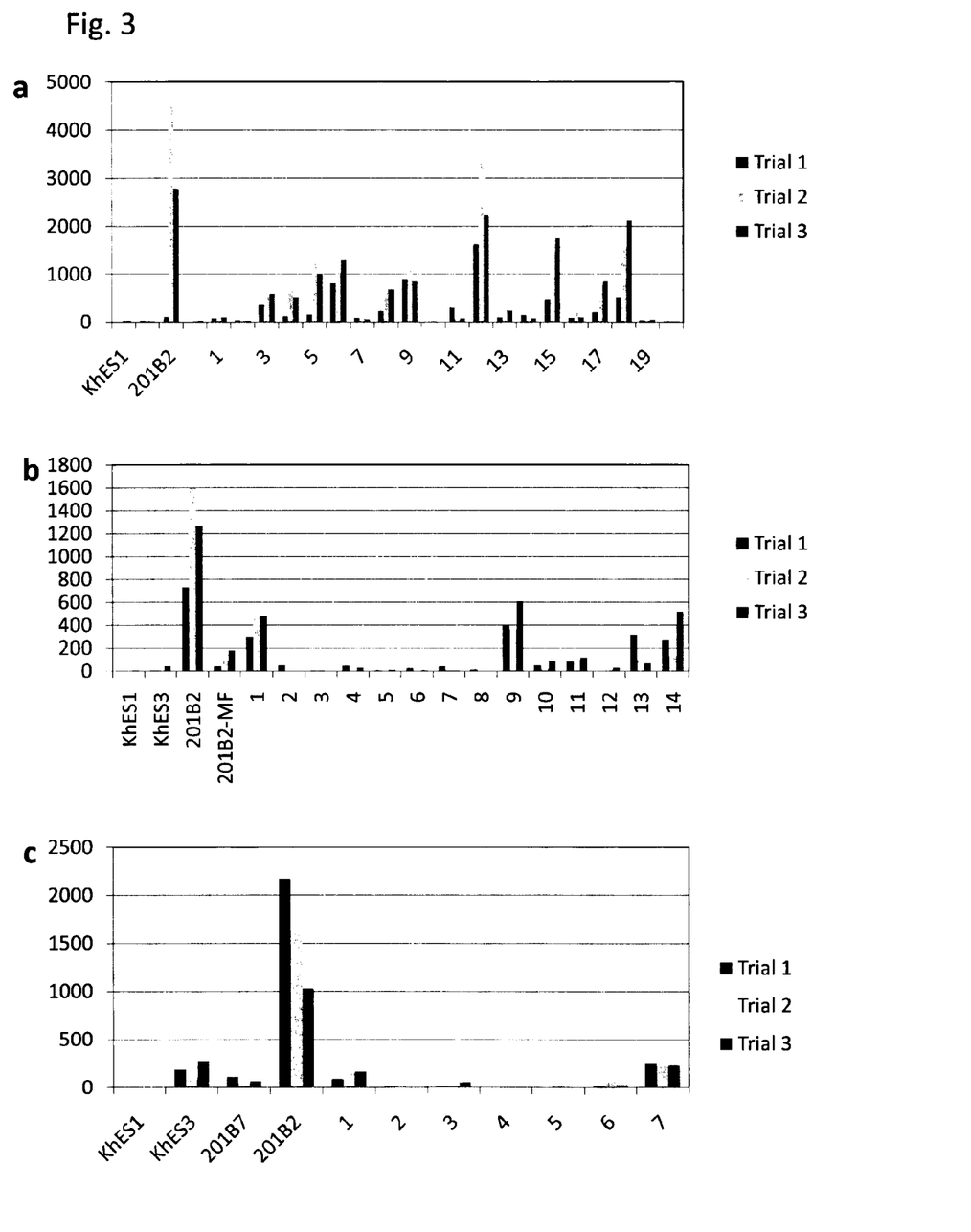

After culturing under undifferentiation maintaining condition, the cells were stained with crystal violet (FIG. 2), and the number of colonies was measured. The results of measurement for the iPS cells established by the four-factor method are shown in Table 2 and FIG. 3a, and the results of measurement for the iPS cells established by the three-factor method are shown in Table 3 and FIG. 3b. Further, the results of measurement for iPS-KhES1-Fib-4F are shown in Table 4 and FIG. 3c.

Based on these results, for the cell lines 201B7, 1, 2, 7, 10, 11 and 20 which were established by the four-factor method, the number of colonies were smaller than those from the control human ES cells.

Similarly, for 2 to 8 and 12 which were established by the three-factor method, the numbers of colonies were smaller than those for the control human ES cells.

iPS-KhES1-Fib-4F showed smaller numbers of colonies formed (1 to 6), compared to human ES cells. On the other hand, 201B2 having a mutation in the karyotype showed a larger number of colonies compared to human ES cells. That is, 201B2 was revealed to be an iPS cell line showing resistance to differentiation induction.

From the above results, it was revealed that human iPS cells having reduced differentiation resistance can be selected by using the present invention.

TABLE 2

|  | Trial 1 | Trial 2 | Trial 3 |
| --- | --- | --- | --- |
| KhES1 | 6 | 115 | 28 |
| KhES3 | 31 | 42 | 23 |
| 201B2 | 111 | 4604 | 2789 |
| 201B7 | 17 | 34 | 38 |
| 1 | 85 | 113 | 106 |
| 2 | 50 | 43 | 43 |
| 3 | 362 | 533 | 596 |
| 4 | 122 | 664 | 523 |
| 5 | 163 | 1254 | 1003 |
| 6 | 812 | 1044 | 1296 |
| 7 | 89 | 109 | 69 |
| 8 | 234 | 772 | 689 |
| 9 | 899 | 1308 | 853 |
| 10 | 13 | 59 | 14 |
| 11 | 308 | 65 | 87 |
| 12 | 1628 | 3336 | 2234 |
| 13 | 104 | 261 | 245 |
| 14 | 145 | 171 | 87 |
| 15 | 479 | 1416 | 1754 |
| 16 | 88 | 213 | 106 |
| 17 | 210 | 775 | 850 |
| 18 | 518 | 1567 | 2125 |
| 19 | 48 | 122 | 56 |
| 20 | 25 | 29 | 23 |

TABLE 3

|  | Trial 1 | Trial 2 | Trial 3 |
| --- | --- | --- | --- |
| KhES1 | 6 | 1 | 9 |
| KhES3 | 10 | 15 | 45 |
| 201B2 | 734 | 1596 | 1268 |
| 201B2-MF | 43 | 95 | 184 |
| 1 | 302 | 503 | 482 |
| 2 | 52 | 0 | 3 |
| 3 | 6 | 13 | 5 |
| 4 | 48 | 2 | 32 |
| 5 | 9 | 3 | 14 |
| 6 | 28 | 4 | 10 |

TABLE 3-continued

|  | Trial 1 | Trial 2 | Trial 3 |
| --- | --- | --- | --- |
| 7 | 42 | 19 | 9 |
| 8 | 17 | 3 | 5 |
| 9 | 410 | 370 | 610 |
| 10 | 52 | 23 | 89 |
| 11 | 86 | 103 | 122 |
| 12 | 1 | 14 | 32 |
| 13 | 320 | 103 | 70 |
| 14 | 270 | 132 | 524 |

TABLE 4

|  | Trial 1 | Trial 2 | Trial 3 |
| --- | --- | --- | --- |
| KhES1 | 5 | 6 | 5 |
| KhES3 | 183 | 103 | 278 |
| 201B7 | 110 | 47 | 66 |
| 201B2 | 2174 | 1627 | 1028 |
| 1 | 92 | 157 | 168 |
| 2 | 10 | 19 | 4 |
| 3 | 16 | 20 | 54 |
| 4 | 3 | 1 | 2 |
| 5 | 2 | 22 | 4 |
| 6 | 15 | 61 | 30 |
| 7 | 261 | 223 | 231 |

Example II

Cells

KhES-1, KhES-3 (Suemori H, et al. *Biochem Biophys Res Commun.* 345:926-32, 2006) and H9 (Thomson, J. A., et al., *Science* 282: 1145-1147, 1998) were used as human ES cells.

Following 9 families and 39 clones were used as human iPS cells.

(i) 4 clones of CB-EP6F were prepared from CD34 positive cells contained in cord blood (WO2010/131747) by induction of 6 factors (OCT3/4, SOX2, KLF4, L-Myc, LIN28 and p53shRNA) with episomal vector (Okita K, et al. Nat Methods. 8:409-12, 2011).

(ii) 3 clones of CB-RE4F were prepared from CD34 positive cells contained in cord blood by induction of 4factors (OCT3/4, SOX2, KLF4 and c-MYC) with retrovirus (WO2010/131747).

(iii) 5 clones of CB-SV4F were prepared from CD34 positive cells contained in cord blood (WO2010/131747) by induction of 4factors (OCT3/4, SOX2, KLF4 and c-MYC) with Sendai virus (Seki T, et al. Cell Stem Cell. 7:11-4, 2010).

(iv) 3 clones of DP-EP6F were prepared from dental pulp stem cells by induction of 6 factors (OCT3/4, SOX2, KLF4, L-Myc, LIN28 and p53shRNA) with episomal vector (Okita K, et al. Nat Methods. 8:409-12, 2011).

(v) 3 clones of FB-EP6F were prepared from skin fibroblasts (Takahashi K, et al. Cell. 131:861-72, 2007) by induction of 6 factors (OCT3/4, SOX2, KLF4, L-Myc, LIN28 and p53shRNA) with episomal vector (Okita K,et al. Nat Methods. 8:409-12, 2011).

(vi) 4 clones of FB-RV3F were prepared from skin fibroblasts by induction of 3 factors (OCT3/4, SOX2 and KLF4) with retrovirus (Nakagawa M, et al. Nat Biotechnol. 26:101-6, 2007).

(vii) 9 clones of FB-RV4F were prepared from skin fibroblasts by induction of 4factors (OCT3/4, SOX2, KLF4 and c-MYC) with retrovirus (Takahashi K, et al. Cell. 131:861-72, 2007).

(viii) 4 clones of PM-EP6F were prepared from T-cells contained in peripheral blood mononuclear cells (PBMC)

(Seki T, et al. Cell Stem Cell. 7:11-4, 2010) by induction of 6 factors (OCT3/4, SOX2, KLF4, L-Myc, LIN28 and p53shRNA) with episomal vector (Okita K,et al. Nat Methods. 8:409-12, 2011).

(ix) 4 clones of PM-SV4F were prepared from T-cells contained in peripheral blood mononuclear cells (PBMC) by induction of 4factors (OCT3/4, SOX2, KLF4 and c-MYC) with Sendai virus (Seki T, et al. Cell Stem Cell. 7:11-4, 2010).

Differentiation Induction

The human ES cells and human iPS cells were induced to differentiate into neural cells with modified SFEBq method comprising following steps of:

(i) the ES or iPS cells were cultured with medium containing Y27632(WAKO);

(ii) to remove feeder cells, CTK dissociation solution (0.25% Trypsin, 1 mg/ml Collagenase and KSR 20%, and 1 mM $CaCl_2$) was added to culture dish and all cells were transferred to gelatin coated dish. Then, the adherent cells were discarded;

(iii) remained ES or iPS cell clusters were dissociated with Accumax (Innovate cell technologies);

(iv) the dissociated ES cells or iPS cells were transferred to LIPIDURE-COAT PLATE (NOF Corporation) to form embryoid body and cultured with differentiation medium (DMEM/Ham's F12 containing 5% KSR(Invitrogen), 2mM L-glutamine(Invitrogen), MEM-non-essential amino acids solution(Invitrogen), 1 μM 2-mercaptoethanol (2-ME), 10 μM Y27632, 2 μM Dorsomorphin (Sigma) and 10 μM SB431542 (Sigma)) for 3 or 4 days; and (v) the cells culturing for more 10 or 11 days with replacement of half the volume of medium with new differentiation medium without Y27632, Dorsomorphin and SB431542 every 3 or 4 days.

Measurement of Content Rate of Undifferentiated Cells

Figure 4:
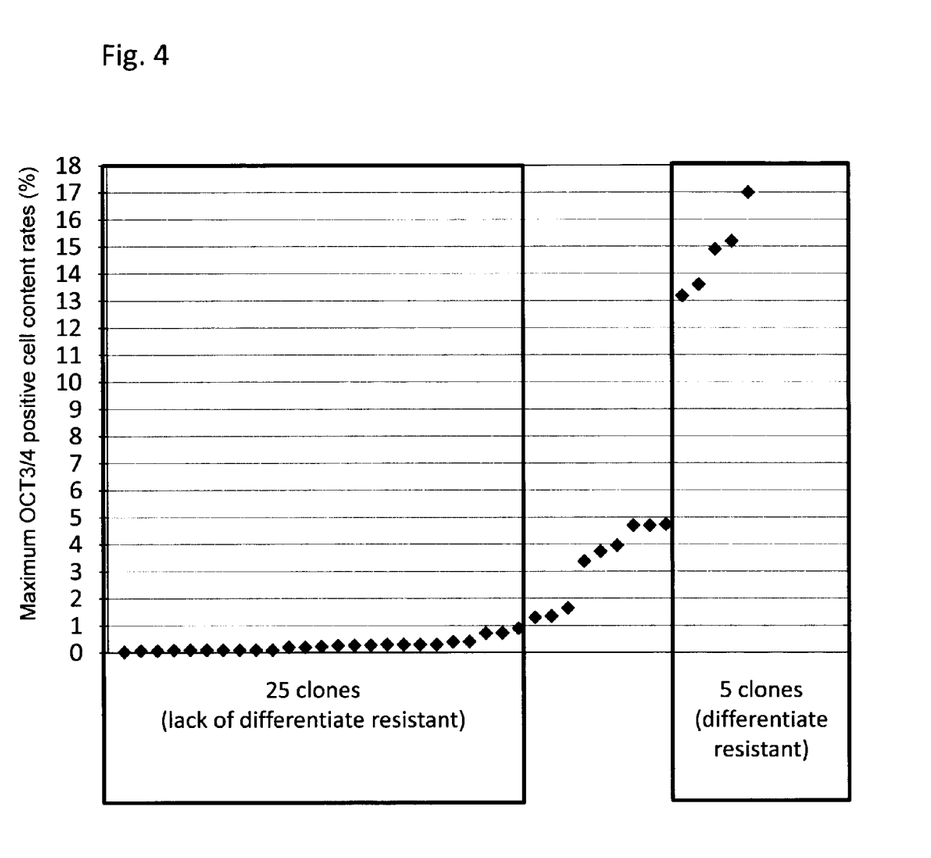
FIG. 4 shows the Oct3/4 positive cell content rate after the neural differentiation from various clones of iPS cells or ES cells.

The obtained neural cells were dissociated and immunostained with Oct3/4 antibody. Then, the content rate of Oct3/4 positive cells was analyzed with flow cytometry. The result is shown in Table 5 and FIG. 4. From the above results, it was revealed that 5 clones of human iPS cells (CB-RV4F-2, DP-EP6F-1, FB-RV3F-3, FB-RV3F-4 and FB-RV4F-5) could be selected as the clones with differentiation resistance. On the other hand, there were 25 clones with low differentiation resistance, whose maximum content rates are not more than 1%.

TABLE 5

| Clone name | Source | Factor | method | 1st | 2nd | 3rd | 4th | 5th | 6th | 7th | 8th | maximum rate |
|---|---|---|---|---|---|---|---|---|---|---|---|---|
| KhES1 | | | | 0.04 | 0.8 | 0.11 | 0.13 | 0.1 | 0.02 | 0.8 | 0.5 | 0.8 |
| KhES3 | | | | 0.2 | | | | | | | | 0.2 |
| H9 | | | | 3.09 | 0.88 | 0.18 | 0.09 | 0.02 | 0.3 | | | 3.09 |
| CB-EP6F-1 | Cord blood | OSKUL + shp53 | Episomal plasmid | 0.3 | | | | | | | | 0.3 |
| CB-EP6F-2 | Cord blood | OSKUL + shp53 | Episomal plasmid | 0.3 | | | | | | | | 0.3 |
| CB-EP6F-3 | Cord blood | OSKUL + shp53 | Episomal plasmid | 0.1 | | | | | | | | 0.1 |
| CB-EP6F-4 | Cord blood | OSKUL + shp53 | Episomal plasmid | 4.7 | | | | | | | | 4.7 |
| CB-RV4F-1 | Cord blood | OSKM | Retro virus | 0.41 | 0.35 | | | | | | | 0.41 |
| CB-RV4F-2 | Cord blood | OSKM | Retro virus | 12.3 | 11.4 | 17 | 10.8 | 14.5 | 12.8 | | | 17 |
| CB-RV4F-3 | Cord blood | OSKM | Retro virus | 0.73 | 0.39 | | | | | | | 0.73 |
| CB-SV4F-1 | Cord blood | OSKM | Sendai virus | 0.9 | 0.7 | 0.7 | | | | | | 0.9 |
| CB-SV4F-2 | Cord blood | OSKM | Sendai virus | 0 | 0.1 | 0.1 | | | | | | 0.1 |
| CB-SV4F-3 | Cord blood | OSKM | Sendai virus | 0.3 | 0.1 | | | | | | | 0.3 |
| CB-SV4F-4 | Cord blood | OSKM | Sendai virus | 0.2 | 0.3 | | | | | | | 0.3 |
| CB-SV4F-5 | Cord blood | OSKM | Sendai virus | 0.1 | 0 | | | | | | | 0.1 |
| DP-EP6F-1 | Dental pulp | OSKUL + shp53 | Episomal plasmid | 11.9 | 13.6 | 4.7 | 6.45 | 3.18 | 4.3 | | | 13.6 |
| DP-EP6F-2 | Dental pulp | OSKUL + shp53 | Episomal plasmid | 0.05 | 0.07 | | | | | | | 0.07 |
| DP-EP6F-3 | Dental pulp | OSKUL + shp53 | Episomal plasmid | 0.07 | 0.09 | | | | | | | 0.09 |
| FB-EP6F-1 | Fibroblast | OSKUL + shp53 | Episomal plasmid | 0.07 | 0.02 | | | | | | | 0.07 |
| FB-EP6F-2 | Fibroblast | OSKUL + shp53 | Episomal plasmid | 0.26 | 0.16 | | | | | | | 0.26 |
| FB-EP6F-3 | Fibroblast | OSKUL + shp53 | Episomal plasmid | 0.27 | 0.05 | | | | | | | 0.27 |
| F8-RV3F-1 | Fibroblast | OSK | Retro virus | 0.03 | 0 | | | | | | | 0.03 |
| F8-RV3F-2 | Fibroblast | OSK | Retro virus | 0.28 | 0.1 | | | | | | | 0.28 |
| F8-RV3F-3 | Fibroblast | OSK | Retro virus | 2.75 | 7.53 | 15.2 | 1.44 | | | | | 15.2 |
| FB-RV3F-4 | Fibroblast | OSK(M) | Retro virus | 1.94 | 13.2 | 7.98 | 8.45 | 14.9 | 9.84 | 4 | | 14.9 |
| FB-RV4F-1 | Fibroblast | OSKM | Retro virus | 0.37 | 0.72 | | | | | | | 0.72 |
| FB-RV4F-2 | Fibroblast | OSKM | Retro virus | 0.15 | 0.23 | 0.02 | 0.01 | | | | | 0.23 |
| FB-RV4F-3 | Fibroblast | OSKM | Retro virus | 2.71 | 3.74 | | | | | | | 3.74 |
| FB-RV4F-4 | Fibroblast | OSKM | Retro virus | 3.38 | 0.06 | | | | | | | 3.38 |
| FB-RV4F-5 | Fibroblast | OSKM | Retro virus | 11.3 | 10.8 | 11.4 | 9.01 | 7.14 | 13.2 | | | 13.18 |
| FB-RV4F-6 | Fibroblast | OSKM | Retro virus | 0.59 | 3.96 | | | | | | | 3.96 |
| FB-RV4F-7 | Fibroblast | OSKM | Retro virus | 4.74 | 0.07 | | | | | | | 4.74 |
| FB-RV4F-8 | Fibroblast | OSKM | Retro virus | 1.65 | 0.09 | | | | | | | 1.65 |
| FB-RV4F-9 | Fibroblast | OSKM | Retro virus | 1.35 | 0.05 | | | | | | | 1.35 |
| PM-EP6F-1 | PBMC | OSKUL + shp53 | Episomal plasmid | 0.1 | | | | | | | | 0.1 |
| PM-EP6F-2 | PBMC | OSKUL + shp53 | Episomal plasmid | 4.7 | | | | | | | | 4.7 |
| PM-EP6F-3 | PBMC | OSKUL + shp53 | Episomal plasmid | 0.2 | | | | | | | | 0.2 |
| PM-EP6F-4 | PBMC | OSKUL + shp53 | Episomal plasmid | 0.1 | | | | | | | | 0.1 |
| PM-SV4F-1 | PBMC | OSKM | Sendai virus | 0.1 | 0.1 | | | | | | | 0.1 |
| PM-SV4F-2 | PBMC | OSKM | Sendai virus | 0.1 | 0.2 | | | | | | | 0.2 |
| PM-SV4F-3 | PBMC | OSKM | Sendai virus | 0.1 | 1.3 | 1.3 | | | | | | 1.3 |
| PM-SV4F-4 | PBMC | OSKM | Sendai virus | 0.1 | 0.2 | 0.4 | | | | | | 0.4 |

Example II

Cells

KhES-1, KhES-3 (Suemori H, et al. *Biochem Biophys Res Commun.* 345:926-32, 2006) and H9 (Thomson, J. A., et al., Science 282 : 1145-1147, 1998) were used as human ES cells.

The human iPS clones (CB-RV4F-2, DP-EP6F-1, FB-RV3F-4 and FB-RV4F-5) which resisted inducing neural differentiation by modified SFEBq method were subcloned into 15 clones, 15 clones, 10 clones and 12 clones, respectively (see table 6 to 9).

Measurement of Content Rate of Undifferentiated Cells

Figure 5:
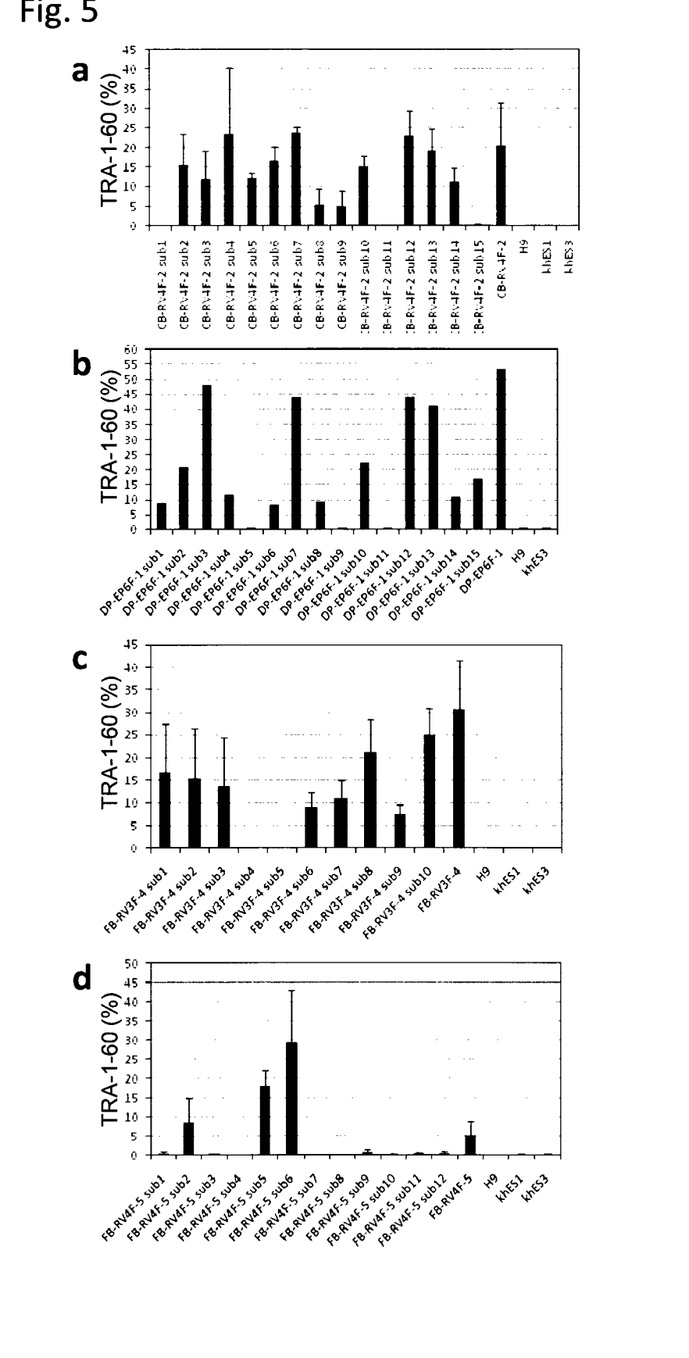
FIG. 5 shows the TRA-1-60 positive cell content rate after the neural differentiation from various clones of iPS cells or ES cells. a represent the results obtained for CB-RV4F-2 subclones. b represent the results obtained for DP-EP6F-1 subclones. c represent the results obtained for FB-RV3F-4 subclones. d represent the results obtained for FB-RV4F-5 subclones.

The neural cells which were produced with above modified SFEBq method from said subclones, parent clones or ES cell lines were dissociated and immunostained with TRA-1-60 antibody. Then, the content rate of TRA-1-60 positive cells was analyzed with flow cytometry. The result is shown in Table 6 to 9 and FIG. 5a to d. From the above results, it was revealed that 16 subclones could be selected as the clones with low differentiation resistance.

TABLE 6

| subclone name | TRA-1-60 positive cells (%) | | | |
|---|---|---|---|---|
| | 1st try | 2nd try | 3rd try | Average |
| CB-RV4F-2 sub1 | 0.1 | 0.1 | 0.1 | 0.1 |
| CB-RV4F-2 sub2 | 24.6 | 10.1 | 11.5 | 15.4 |
| CB-RV4F-2 sub3 | 17.2 | 14.7 | 4.2 | 12.03333 |
| CB-RV4F-2 sub4 | 8.4 | 20 | 41.8 | 23.4 |
| CB-RV4F-2 sub5 | 12 | 13.8 | 11 | 12.26667 |
| CB-RV4F-2 sub6 | 20.7 | 15 | 14 | 16.56667 |
| CB-RV4F-2 sub7 | 25.1 | 21.8 | 24.1 | 23.66667 |
| CB-RV4F-2 sub8 | 10 | 4.6 | 2 | 5.533333 |
| CB-RV4F-2 sub9 | 9.6 | 3.5 | 1.9 | 5 |
| CB-RV4F-2 sub10 | 17.5 | 11.8 | 15.5 | 14.93333 |
| CB-RV4F-2 sub11 | 0.1 | 0.3 | 0.1 | 0.166667 |
| CB-RV4F-2 sub12 | 28.8 | 23.8 | 15.7 | 22.76667 |
| CB-RV4F-2 sub13 | 23.1 | 21.5 | 12.1 | 18.9 |
| CB-RV4F-2 sub14 | 14.2 | 7.3 | 11.8 | 11.1 |
| CB-RV4F-2 sub15 | 0 | 0.5 | 0.1 | 0.2 |
| CB-RV4F-2 | 27.3 | 26 | 8 | 20.43333 |
| H9 | 0.2 | 0.1 | 0.2 | 0.166667 |
| khES1 | 0 | 0 | 0.3 | 0.1 |
| khES3 | 0.1 | 0 | 0.1 | 0.066667 |

TABLE 7

| subclone name | TRA-1-60 positive cells (%) |
|---|---|
| DP-EP6F-1 sub1 | 8.8 |
| DP-EP6F-1 sub2 | 21 |
| DP-EP6F-1 sub3 | 48.3 |
| DP-EP6F-1 sub4 | 11.4 |
| DP-EP6F-1 sub5 | 0.6 |
| DP-EP6F-1 sub6 | 8.1 |
| DP-EP6F-1 sub7 | 43.9 |
| DP-EP6F-1 sub8 | 9.5 |
| DP-EP6F-1 sub9 | 0.2 |
| DP-EP6F-1 sub10 | 22 |
| DP-EP6F-1 sub11 | 0.1 |
| DP-EP6F-1 sub12 | 44.1 |
| DP-EP6F-1 sub13 | 41.3 |
| DP-EP6F-1 sub14 | 10.9 |
| DP-EP6F-1 sub15 | 16.9 |
| DP-EP6F-1 | 53.5 |
| H9 | 0.1 |
| khES3 | 0.1 |

TABLE 8

| subclone name | TRA-1-60(%) | | | |
|---|---|---|---|---|
| | 1st try | 2nd try | 3rd try | Average |
| FB-RV3F-4 sub1 | 10.9 | 29.1 | 9.9 | 16.63333 |
| FB-RV3F-4 sub2 | 9.4 | 28.3 | 8.5 | 15.4 |
| FB-RV3F-4 sub3 | 7.7 | 26 | 6.7 | 13.46667 |
| FB-RV3F-4 sub4 | 0 | 0.1 | 0 | 0.033333 |
| FB-RV3F-4 sub5 | 0.1 | 0 | 0 | 0.033333 |
| FB-RV3F-4 sub6 | 6.7 | 12.9 | 7.5 | 9.033333 |
| FB-RV3F-4 sub7 | 14 | 12.5 | 6.6 | 11.03333 |
| FB-RV3F-4 sub8 | 12.9 | 25.9 | 24.8 | 21.2 |
| FB-RV3F-4 sub9 | 7.5 | 9.5 | 5.2 | 7.4 |
| FB-RV3F-4 sub10 | 21.4 | 32 | 21 | 24.8 |
| FB-RV3F-4 | 30.8 | 41.4 | 19.9 | 30.7 |
| H9 | 0.1 | 0 | 0.1 | 0.066667 |
| khES1 | 0.1 | 0.1 | 0 | 0.066667 |
| khES3 | 0 | 0.1 | 0 | 0.033333 |

TABLE 9

| subclone name | TRA-1-60 positive cells (%) | | |
|---|---|---|---|
| | 1st try | 2nd try | Average |
| FB-RV4F-5 sub1 | 0.1 | 0.8 | 0.45 |
| FB-RV4F-5 sub2 | 3.8 | 13.1 | 8.45 |
| FB-RV4F-5 sub3 | 0.3 | 0.5 | 0.4 |
| FB-RV4F-5 sub4 | 0.1 | 0.1 | 0.1 |
| FB-RV4F-5 sub5 | 14.8 | 20.9 | 17.85 |
| FB-RV4F-5 sub6 | 38.9 | 19.6 | 29.25 |
| FB-RV4F-5 sub7 | 0.1 | 0 | 0.05 |
| FB-RV4F-5 sub8 | 0.1 | 0.2 | 0.15 |
| FB-RV4F-5 sub9 | 0.2 | 1.3 | 0.75 |
| FB-RV4F-5 sub10 | 0.4 | 0.1 | 0.25 |
| FB-RV4F-5 sub11 | 0.2 | 0.7 | 0.45 |
| FB-RV4F-5 sub12 | 0.1 | 0.8 | 0.45 |
| FB-RV4F-5 | 2.8 | 7.7 | 5.25 |
| H9 | 0.2 | 0.1 | 0.15 |
| khES1 | 0.1 | 0.3 | 0.2 |
| khES3 | 0.1 | 0.3 | 0.2 |

The invention claimed is:

1. A method for selecting human induced pluripotent stem (iPS) cells having reduced differentiation resistance, said method comprising the steps of: (1) inducing differentiation of human iPS cells in said population;
   (2) detecting remaining undifferentiated cells after the step (1) and determining the percentage of said undifferentiated cells in said population, wherein the undifferentiated cells are detected by measurement of undifferentiated cell marker selected from the group consisting of S SEAA-3, S SEA-4, TRA-1-60, TRA-1-81, OCT3/4, Nanog, and Rex 1; and
   (3) (i) determining said population as having reduced differentiation resistance when the percentage of remaining undifferentiated cells detected in step (2) is equivalent to or not more than the percentage of remaining undifferentiated cells after induction of differentiation in reduced differentiation resistant human embryonic stem cells H9, KhES1 or KhES3, or
   (ii) determining said population as having reduced differentiation resistance when the percentage of remaining undifferentiated cells detected in step (2) is not more than 4.7%.

2. The method according to claim 1, wherein differentiation induction in step (1) is performed by culturing human iPS cells without using feeder cells.

3. The method according to claim 2, wherein differentiation induction in step (1) is performed by culturing human iPS cells in N2B27 medium.

4. The method according to claim 3, wherein differentiation induction in step (1) is performed by culturing human iPS cells in N2B27 medium for 5 days.

5. The method according to claim 1, wherein differentiation induction in the step (1) is induction of differentiation to neural cells.

6. The method according to claim 5, wherein the induction of differentiation to neural cells is performed by culturing human iPS cells with formation of embryoid bodies in serum free conditions.

7. The method according to claim 6, wherein the induction of differentiation to neural cells is performed by culturing human iPS cells in culture medium comprising BMP inhibitor and TGFβ family inhibitor.

8. The method according to claim 7, wherein the BMP inhibitor is Dorsomorphin or LDN-193189, and the TGFβ family inhibitor is SB431542 or A-83-01.

9. The method according to claim 1, wherein the percentage of remaining undifferentiated cells detected in step (2) is not more than 1%.

* * * * *

UNITED STATES PATENT AND TRADEMARK OFFICE
CERTIFICATE OF CORRECTION

| | | Page 1 of 1 |
|---|---|---|
| PATENT NO. | : 8,932,857 B2 | |
| APPLICATION NO. | : 13/704584 | |
| DATED | : January 13, 2015 | |
| INVENTOR(S) | : Shinya Yamanaka et al. | |

It is certified that error appears in the above-identified patent and that said Letters Patent is hereby corrected as shown below:

In the Specification

In column 4 at line 2, Change "at 2 0" to --at--.

In column 5 at line 13, Change "lymphotrophic" to --lymphotropic--.

In column 7 at lines 55-56, Change "(www.plozone.org)," to --(www.plosone.org),--.

Signed and Sealed this
Twenty-ninth Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,932,857 B2
APPLICATION NO. : 13/704584
DATED : January 13, 2015
INVENTOR(S) : Shinya Yamanaka et al.

Page 1 of 2

It is certified that error appears in the above-identified patent and that said Letters Patent is hereby corrected as shown below:

IN THE CLAIMS

In column 16 at lines 40-61, In Claim 1 change "1. A method for selecting human induced pluripotent stem (iPS) cells having reduced differentiation resistance, said method comprising the steps of: (1) inducing differentiation of human iPS cells in said population;

(2) detecting remaining undifferentiated cells after the step (1) and determining the percentage of said undifferentiated cells in said population, wherein the undifferentiated cells are detected by measurement of undifferentiated cell marker selected from the group consisting of SSEAA-3, S SEA-4, TRA-1-60, TRA-1-81, OCT3/4, Nanog, and Rex 1; and (3) (i) determining said population as having reduced differentiation resistance when the percentage of remaining undifferentiated cells detected in step (2) is equivalent to or not more than the percentage of remaining undifferentiated cells after induction of differentiation in reduced differentiation resistant human embryonic stem cells H9, KhES1 or KhES3, or (ii) determining said population as having reduced differentiating resistance when the percentage of remaining undifferentiated cells detected in step (2) is not more than4.7%." to
--1. A method for determining a population of human induced pluripotent stem (iPS) cells as having reduced differentiation resistance, said method comprising: (1) inducing differentiation of the human iPS cells in said population;

(2) detecting remaining undifferentiated cells in said population after step (1) and determining the percentage of said undifferentiated cells in said population, wherein the undifferentiated cells are detected by measurement of undifferentiated cell marker selected from the group consisting of S SEAA-3, S SEA-4, TRA-1-60, TRA-1-81, OCT3/4, Nanog, and Rex 1; and (3) (i) determining said population as having reduced differentiation resistance when the percentage of remaining undifferentiated cells detected in step (2) in equivalent to or not more than the Signed and Sealed this
Tenth Day of November, 2015

Michelle K. Lee
*Director of the United States Patent and Trademark Office* percentage of remaining undifferentiated cells after induction of differentiation in reduced differentiation resistant human embryonic stem cells H9, KhES1 or KhES3, or (ii) determining said population as having reduced differentiation resistance when the percentage of remaining undifferentiated cells detected in step (2) in not more than 4.7%.--.

In column 17 at lines 11-14, In Claim 7 change "7. The method according to claim 6, wherein the induction of differentiation to neural cells is performed by culturing human iPS cells in culture medium comprising BMP inhibitor and TGFβ family inhibitor." to --7. The method according to claim 6, wherein the induction of differentiation to neural cells is performed by culturing human iPS cells with formation of embryoid bodies in serum-free conditions.--.